(12) United States Patent
Kwiatkowski et al.

(10) Patent No.: US 6,291,669 B1
(45) Date of Patent: Sep. 18, 2001

(54) SOLID PHASE SYNTHESIS

(76) Inventors: Marek Kwiatkowski, Lövsångarvägen 17, S-756 52 Uppsala; Mats Nilsson, Polhemsgatan 36, S-112 30 Stockholm; Ulf Landegren, Eksoppsvägen 16, S-756 46 Uppsala, all of (SE)

( * ) Notice: Subject to any disclaimer, the term of this patent is extended or adjusted under 35 U.S.C. 154(b) by 0 days.

(21) Appl. No.: 09/254,048
(22) PCT Filed: Aug. 27, 1997
(86) PCT No.: PCT/SE97/01418
§ 371 Date: Jul. 19, 1999
§ 102(e) Date: Jul. 19, 1999
(87) PCT Pub. No.: WO98/08857
PCT Pub. Date: Mar. 5, 1998

(30) Foreign Application Priority Data

Aug. 30, 1996 (SE) .................................................. 9603171

(51) Int. Cl.$^7$ ............................. C07H 21/00; C07F 7/21; C07F 9/02
(52) U.S. Cl. .................. 536/25.3; 536/25.31; 536/25.33; 536/25.34; 556/404; 556/407; 556/425
(58) Field of Search .............................. 536/25.3, 25.33, 536/25.34, 25.31; 556/404, 407, 425

(56) References Cited

U.S. PATENT DOCUMENTS 5,214,134 * 5/1993 Weis et al. .
5,589,586 * 12/1996 Holmberg .

FOREIGN PATENT DOCUMENTS

WO 92/04364 3/1992 (WO) .
WO 92/09615 6/1992 (WO) .
WO 93/13220 7/1993 (WO) .

OTHER PUBLICATIONS

J. Olejnik et al., "Photocleavable biotin phosphoramidite for 5'–end labeling, affinity purification and phosphorylation of synthetic oligonucleotides," Nucleic Acids, Res. Jan. 15; 24(2): pp. 361–366. No Year.
William H. McClain et al., "Variants in clones of gene–machine–synthesized oligodeoxynucleotides," Nucleic Acids Research, vol. 14, No. 16, (1986), p. 6770.
Bernard A. Connolly, "Solid Phase 5'–Phosphorylation of Oligonucleotides," Tetrahedron Letters, vol. 28, No. 4, (1987), pp. 463–466.
Thomas Horn and Mickey S. Urdea, "Solid supported hydrolysis of apurinic sites in synthetic oligonucleotides for rapid and efficient purification on reverse–phase cartridges," Nucleic Acids Research, vol. 16, No. 24, (1996), pp. 11559–11571.
Willi Banworth et al., "A New Combined Purification/Phosphorylation Procedure for Oligodeoxynucleotides," Helvetica Chimica Acta, vol. 73, (1990), pp. 1139–1147.
Mats Nilsson et al., "Padlock Probes: Circularizing Oligonucleotides for Localized DNA Detection," Science, vol. 265, Sep. 30, 94, pp. 2085–2088.
Matthew J. Plunkett et al., "A Silicon–Based Linker for Traceless Solid–Phase Synthesis," J. Org. Chem., vol. 60, No. 19, (1995), pp.6005–6007.
Karen L. Fearon et al., "Investigation of the 'n–1' impurity in phosphorothioate oligodeoxynucleotides synthesized by the solid–phase β–cyanoethyl phosphoramidite method using stepwise sulfurization," Nucleic Acids Research, vol. 23, No. 14, (1995), pp. 2754–2761.
Jamal Temsamani et al., "Sequence identity of the n–1 product of a synthetic oligonucleotide," Nucleic Acids Research, vol. 23, No. 11, (1995), pp. 1841–1844.
P. Agback et al., "The differences in the $T_2$ relaxation rates of the protons in the partially–deuteriated and fully protonated sugar residues in a large oligo–DNA ('NMR–window') gives complementary structural information," Nucleic Acids Research, vol. 22, No. 8, (1994), pp. 1404–1412.
R.B. Merrifield, "Solid Phase Peptide Synthesis. I. The Synthesis of a Tetrapeptide," Journal of the American Chemical Society, vol. 85, No. 13, Jul. 5, (1963), pp. 2149–2154.
Richard T. Pon, "Solid–Phase Supports for Oligonucleotide Synthesis," Methods in Molecular Biology, vol. 20, No. 19, (1993), pp. 465–496.
Michael Nassel, "Total chemical synthesis of a gene for hepatitis B virus core protein and its functional characterization," Gene, 66, (1998), pp. 279–274.

* cited by examiner

Primary Examiner—James O. Wilson
(74) Attorney, Agent, or Firm—Fish & Richardson P.C., P.A.

(57) ABSTRACT

The present invention relates to a support system for solid phase synthesis of oligomers, such as oligonucleotides, wherein the starting compound is bound to the support via a disiloxyl linkage. Furthermore, the invention relates to a method for synthesis of oligonucleotides on a solid support. The support system comprises a stable disiloxyl linkage providing high nucleoside loadings to the support and the method allows convenient non-laborious oligomer synthesis.

15 Claims, 3 Drawing Sheets

SOLID PHASE SYNTHESIS

TECHNICAL FIELD

The present invention relates to a support system for solid phase synthesis of oligomers, such as oligonucleotides. Furthermore, the invention relates to a method for synthesis of oligonucleotides on a solid support.

BACKGROUND OF THE INVENTION

Oligonucleotides are polymers built up by polycondensation of ribonucleoside (RNA) or deoxyribonucleoside (DNA) phosphates.

Oligonucleotides can be assembled by repetitive addition of nucleotide monomer using solid-phase methods. Since the introduction of solid-phase synthesis [R. B. Merrifield, J. Am. Chem. Soc. 85 (1963) 2149], the following requirements have been worked out: (1) The solid support must be insoluble and preferably unswellable in the solvent used. (2) Functional groups on the solid support must allow covalent binding of the first nucleoside in a reproducible manner. (3) The solid support must be chemically inert to all reagents used during synthesis and deprotection. The most commonly used supports are controlled pore glass beads (CPG), silica, or polystyrene beads.

Below the synthesis cycle of the commonly used phosphoramidite method is described:

1. Deprotection of the 5'-hydroxyl group in order to generate the parent hydroxyl compounds. This is normally done by treatment of the support with di- or trichloroacetic acid in an organic solvent (for removal of protecting groups)

2. The support is washed in order to remove traces of acid.

3. The 5'-hydroxyl group is reacted with the 3'-phosphoramidite moiety of properly protected incoming nucleotide (A, C, G or T) in the presence of an activator (e.g. tetrazole) to form a 3'-5'-phosphite triester.

4. Excess reagents are removed by washing with an appropriate solvent.

5. Unreacted 5'hydroxyl groups are blocked as acetates (capping).

6. The capping reagent is removed by washing.

7. The phosphite triester is then oxidized to the corresponding phosphate triester. This is normally done by the action of aqueous iodine.

8. The oxidation reagents are removed by washing.

The process is repeated until the desired oligonucleotide sequence has been synthesized. After synthesis, all protecting groups are removed and the oligonucleotide is cleaved from the solid support.

In the synthesis, defective oligonucleotides are produced as a consequence of several effects, prominently premature termination of synthesis, followed by capping, which results in 5' truncated molecules, and depurination during the synthetic cycles that is followed by strand scission during deprotection. Recently, attention has also been directed at the appearance of shorter, internally deleted products—so called n-1 and n-2 fragments [Temsamani et al, (1995 ), Nucleic Acids Research 23 (11), 1841–1844]; [Fearon et al, (1995) Nucleic acids Res., 23 (14), 2754–2761].

The need for pure oligonucleotides is exemplified by the requirement for high quality products in antisense therapy [Gelfi et al, (1996), Antisense and Nucleic Acid Drug Development, 6, 47–53], in routine diagnostics applications, or for physicochemical and structural studies [Agback et al, (1994) Nucleic Acids Res, 22 (8), 1404–12]. Also in molecular cloning impure oligonucleotides frequently reduce efficiency and complicate interpretation of results [McClain et al, (1986) Nucleic Acids Res. 14 (16), 6770]; [Nassal, (1988) Gene, 66 (2), 279–94].

Preparative gel electrophoresis provides the best resolution for purification of oligonucleotides. The method is however laborious, often leading to considerable loss of material, and it is poorly suited for automation and scale-up.

Chromatographic separation can solve some of these problems, offering a potential for scale-up with minimal losses and using fully automatized instruments. These positive aspects are off-set by the rather poor resolving power of most chromatographic systems. As a partial solution to this problem chromatographic separation of oligonucleotides labeled with affinity tags has been used. The commonly used trityl-on oligonucleotide separation on reversed-phase columns, or capture of 5'-thiol labelled or biotinylated oligonucleotides on respective thiol-affinity [Bannwarth et al, (1990), Helv. Chim. Acta, 73, 1139–1147] or avidin columns [Olejnik et al, (1996), 24 (2), 361–366] offer the possibility to isolate fragments with intact 5'-ends. However, the 5' part of depurinated molecules notoriously contaminate oligonucleotides purified by this method.

A mild basic system has been proposed for partial deprotection and cleavage of apurinic-sites with the oligonucleotides still bound to the solid support. In this manner the 5' ends of depurinated molecules can be discarded before the oligonucleotides are released from the support, followed by isolation of molecules with intact 5' ends [Horn et al, (1988), Nucleic acids Res, 16 (24), 11559–71]. In practice, this strategy was accompanied by a substantial loss of products, due to inadvertent release of oligonucleotides during cleavage of depurinated sites.

In WO92/09615 there is described the use of an alkoxysilyl group as a linker of the oligonucleotide to the support. This linker is inert during the synthetic cycles and it resists conditions that cleave apurinic sites. The linker is finally cleaved from the solid support with tetra butyl ammonium fluoride (TBAF) to obtain, after reversed-phase separation of DMTr-containing material, an oligonucleotide with both 3'- and 5'- ends intact. However, synthesis of this support was laborious and inconvenient. Due to low reactivity of the functional group of the linker the degree of substitution of the support becomes low which leads to insufficient nucleoside loadings of the support. Thus, this method is not suitable for preparation of support useful for large scale synthesis.

SUMMARY OF THE INVENTION

According to a first aspect, the invention provides a support system for solid phase synthesis of oligomers. The support system comprises a support, a linker and a starting compound of the oligomer. The starting compound is bound to the support via a disiloxyl linkage. The disiloxyl function is linked to a hydroxyl group on the support. The functional groups connected to the disiloxyl group are very reactive allowing for reproducible and controlled loading of the starting compounds.

The support system of the invention is easier to produce compared to prior art systems and provides for high loadings to the support. According to the invention high loading values are obtained for the starting nucleoside. These loadings, often higher than 200 $\mu$mol/g, are required for cost-effective large scale synthesis.

The linkage is inert during the synthesis cycles and resists conditions that cleave apurinic sites.

In a preferred embodiment, the starting compound is a nucleoside and the solid phase synthesis is used for the synthesis of oligonucleotides.

Supports with immobilized oligonucleotides can be used as hybridization affinity matrices. Some possible applications of such supports are: purification of DNA-binding proteins, affinity purification of plasmids, as a support for gene assembly (from oligonucleotides) and for diagnostic purposes, etc.

In the new support system of the present invention the first nucleoside is bound to the support via a disiloxyl linkage and the system is preferably represented by the following formula (I)

Formula (I)

wherein B is a ribonucleoside or deoxyribonucleoside base; $R_2$ is —H, —OH, or $OR_7$ in which $R_7$ is a protecting group; $R_1$ protecting group: $R_3$, $R_4$, $R_5$, $R_6$ taken separately each represent alkyl, aryl, cycloalkyl, alkenyl, aralkyl, cycloalkylalkyl, alkyloxy, aryloxy, cycloalkyloxy, alkenyloxy and aralkyloxy; Supp is a solid support: X is an anchoring group used for covalent bonding to the support; $(p-Y)_n$ and $(p-Z)_m$ are oligophosphotriester linkers, wherein p represents a phosphotriester, Y and Z are independently selected from a nucleoside and a rest of a diol, A is an alifatic or aromatic group, n is a number between 0–50, preferably 0–10, and k, l, m are each a number of 0 or 1, with the proviso that when m and n are 0 then 1 and k are 0 and with the proviso that when m=1 then k is 0 and X is O or S.

The protecting groups R1 and $R_7$ are protecting groups usually used for protection of 5' and 2' position of ribo and deoxiribonucleosides. $R_1$ may bee selected from a trityl, monomethoxy trityl, dimethoxytrityl, pixyl or other higher alkoxy-substituted trityl- protecting groups. $R_7$ may bee selected from tertbutyldimehylsilyl (TBDMS), methoxytetrahydropyranoyl (MTHP), tetrahydropyraranoyl, methyl or allyl.

In a preferred embodiment of the invention $R_3$, $R_4$, $R_5$, $R_6$ are isopropyl. The choice of $R_3$, $R_4$, $R_5$, $R_6$ is dictated by stability vs. lability requirements of the disiloxyl linker. It is known that these properties can easily be controlled by modifying electron donating parameters of the substituents.

X can be any anchoring group, preferably O, S or an amide function, provided it is stable to the conditions used under synthesis and the reagent to cleave apurinic sites. The same proviso applies also to the $(p-Y)_n$ linker and $(p-Z)_m$. Thus, there are no other restrictions on Y and Z.

Z is exemplified by a tetraethylene glycol residue.

A wide range of porous as well a non-porous solid supports can be used as supports in methods according to the present invention. The group of preferred supports includes cross linked polystyrenes, silica, polysaccharides, crosslinked polysaccharides and various glasses.

When the oligophosphotriester linker $(p-Y)_n$ is present in the above formula a support is provided resulting in even greater oligonucleotide purity than without said linker. By preparing the supports through a series of synthetic cycles before addition of the cleavable disiloxyl linker and synthesis of the desired oligonucleotide, any nonspecific sites of synthesis will be neutralized. This linker gives improved contact between the starting nucleoside and an incoming reagent and ensures that also oligonucleotides starting from sites not intended for synthesis on the support none the less contribute to the production of the desired oligonucleotide.

According to a second aspect the invention provides a method for oligonucleotide synthesis on a solid support Supp. The method comprises the steps:

(i) preparing a support system as defined above;
(ii) condensation of nucleotides onto the first nucleoside of the support system to synthesize and oligonucleotide;
(iii) removal of all protecting groups on the oligonucleotide except the 5' group, and cleavage of apurinic sites formed during acid-catalysed deprotection;
(iv) cleavage of the full length product from the support; and
(v) purification of the oligonucleotide.

In step (i) an oligophosphotriester linker $(p-Y)_n$ is synthesized on the solid support and a starting nucleoside is bound to the linker via a $(p-z)_m$ linker and a disiloxyl group.

According to one embodiment of the method, the disiloxyl linkage is cleaved selectively according to known methods (Markiewicz W. T., 1979, Journal of Chemical Reserche (M) 0181–0197) with a compound containing fluoride ions, before step (v). A preferred fluoride containing compound is tetra alkyl ammonium fluoride. Trityl ammonium hydrogene fluoride is also suitable. The purification is performed by reversed phase chromatography: using the 5'-protecting group as an affinity handle.

According to an alternative embodiment of the method according to the invention, step (v) is performed by exonuclease treatment whereby non-protected oligonucleotides will be digested. This embodiment is especially suitable for in situ synthesis where chromatography is not possible.

DETAILED DESCRIPTION OF THE INVENTION

The invention will be described more closely below in association with an experimental part and the accompanying drawings, in which

FIG. 2 shows the results of synthesis of a purine rich $(GA)_{40}$ oligonucleotide. A) A reverse phase HPLC chromatogram showing the trityl containing material. The product from a standard support appears as a much broader peak with a large proportion of material appearing later compared to the sharp and symmetrical peak from the novel support. B) Products collected from the peaks in A were 5' labelled and separated on a denaturing polyacrylamide gel. An autoradiogram showing the oligonucleotide obtained using a standard support on the top and material synthesized on the novel support below. C and D) The same gel as in B was scanned on a Phosphorimager (Molecular Dynamics). The data are presented as line graphs with standard support in C and the novel support in D. The n-1 and n-2 peaks are marked in C.

FIG. 3 shows circularization of a 91-mer padlock probe. The term "padlock probe" means a probe which is able to circularize on its target sequence and is described in Nilson, M., Malmgren, H., Samiotaki, M., Kwiatkowski, M., Chowdahry, B. P. And Landergren U. (1994) Science, 265 (5181), 2085–8, to which reference is made. The oligonucleotide was labelled at the 5'-end and the two ends were ligated using an excess of a complementary oligonucleotide as template. The reaction was performed for several cycles of denaturation and ligation using a thermostable ligase. Lane 1: no ligase. Lanes 2, 3 and 4: 1, 2 and 3 cycles of ligation, respectively. All full length (n) oligonucleotides were circularized in the first round of ligation.

The preparation of the support system according to the invention can be performed according to scheme 1 illustrated below:

A disiloxyl residue was applied as a stable linker function between a nucleoside and a solid support. The reactive intermediates (3) or (5) were synthesized in one or three steps, respectively according to Scheme 1 above.

No attempts were made to isolate intermediate (3), therefore silylation of appropriately protected nucleosides (1) were performed using only a slight excess of (2). The addition of an excess of an 13-atoms long chain diol (tetraethyleneglycol) resulted in the formation of an unsymmetrical disiloxyl derivative (4), used subsequently for the synthesis of phosphoroamidite (5).

SCHEME 1

This procedure comprises the following steps:

1. Silylation of the 5'-dimethoxytritylated and appropriately protected nucleosides using 1,3-dichloro-1,1,3,3-tetraisopropyl disiloxane in dry pyridine with addition of imidazol.
2. Reacting of the formed monochloroderivative (3) with an diol e.g. tetraethylene glycol to obtain derivative (4).
3. Introduction of phosphoramidite function to the free hydroxyl group located at the end of the 3'-linker.

According to the invention the homobifunctional, readily available reagent 1,3-dichloro-1,1,2,2-tetraisopropyl disiloxane (2) (scheme 1) was used. In other words, the reagent used in the present invention has two reactive functions which enables high and controllable substitution.

The invention requires a support functionalized with hydroxyl groups linked to the support through nonhydrolyzable bonds. Mono R, hydroxyalkyl-derivatized polystyrene particles (from Pharmacia) was used without modifications. Derivatization of CPG proceeded according to Scheme 2, below.

SCHEME 2 a) thionyl chloride, ethanol; b) γ-butyrolacton, triethylamine;
c) dimethoxytrityl chloride, pyridine; d) NaOH, triethylamine,
e) isobutyl chloroformate; f) aminopropyl-CPG This scheme includes the following reactions:
a) refluxing of 6-aminohexanoic acid in dry ethanol with addition of thionyl chloride to achieve esterification of carboxyl group.
b) acylation of the amino group with γ-butyrolactone to form compound (8).
c) protection of the introduced hydroxyl group with dimethoxytrityl group performed by DMTrCl in dry pyridine.
d) hydrolysis of the ester group with NaOH and formation of the triethylammonium salt of the resulting acid.

e) activation of the carboxyl group by preparing a mixed anhydride upon addition of isobutyl chloroformate.
f) coupling of the activated reagent to the CPG support derivatized with amino functions to form support (12).

The CPG was activated by conventional aminopropylsilanizing [Pon, (1993) In Agraval, S. (ed.), Methods in Molecular Biology. Protocols for oligonucleotides and Analogs. Humana Press Inc. ]. Prior to further derivatization, the amino CPG support was treated with trichloracetic acid in dichlormethane according to Pon [Pon, (1993), supra]. Compound (10) was prepared in high yield starting from an inexpensive 6aminohexanoic acid andy-butyrolacton. It was conveniently converted to the mixed anhydride (11) in a reaction with isobutylchloroformate, and immediately used for coupling to CPG, see Scheme 2. Using different ratios of (11) and a solid support, loadings ranging from 15 to 60 $\mu$ mol/g were obtained. The derivatized support was exhaustively capped with acetic anhydride and silanized with trimethylsilylchloride, TMSCl.

EXPERIMENTAL PROCEDURES

Controlled-pore glass (CPG) (1000 Å) was obtained from CPG Inc. (Fairfield, USA) and was aminopropylsilanized according to Pon et al. [Pon, 1993, supra]. Crosslinked polystyrene particles ( $\mu$m diameter ) derivatized with hydroxylalkyl functions (Mono R) (From Pharmacia, Uppsala, Sweden).

Oligonucleotide syntheses were performed either on an ABI 394 DNA (Pharmacia Biotech AB) instrument. Analytical liquid chromatography of the synthesized oligonucleotides was performed on a Hitachi-Merck La Chrom HPLC system equipped with a LiChrospher RP 18 (5 mm) column (Merck) and using a linear gradient of solvent A: acetonitrile 5% v/v in triethylammonium acetate 0.1 M, pH 7.0 and solvent B: acetonitrile 40% v/v in triethylammonium acetate 0.1 M, pH 7.0. Preparative separations were made on an FPLC system (Pharmacia Biotech AB) using a reversed-phase Pep RPC 10/10 column (Pharmacia) and the above solvent gradient.

EXAMPLE 1

Synthesis of Nucleoside Derivatives

5'-Dimethoxytrityl -3' O-1,1,3,3,-tetraisopropyl-3-tetraethylen-glycoloxy-disiloxyl thymidine (4) (B=T).

5'-DMTr-thymidine (1) (1.30 g, 2.3 mmol) and imidazol (0.32 g, 4.8 mmol) were dried by coevaporation with dry pyridine and dissolved in 20 ml of dry pyridine. 1,3-Dichloro-1,1,3,3-tetraisopropyl disiloxane (2) (0.75 g, 2.4 mmol) was added and the mixture was stirred at 20° C. for 3 hrs to achieve complete consumption of starting material. Tetraethylen glycol (3.9 g, 23 mmol) was added to the formed compound (3) (see Scheme 1) and the mixture was stirred for 6 hrs. Pure compound (4) was isolated as an oil (1.62 g, 72%), following standard bicarbonate work-up, extraction with dichloromethane, evaporation of the organic phase, and flash column chromatography. $^1$H-NMR (CDCl$_3$): 0.85–1.05 (m, 28 H), 1.43 (s, 3 H), 2.25–2.42 (m, 2 H), 2.85 (s, broad, 1 H), 3.27–3.52 (dd, 2 H), 3.54–3.76 (m, 12 H), 3.79 (s, 3 H), 3.80–3.85 (m, 2 H), 4.09 (m, 1 H), 4.68 (m, 1 H), 6.40 (t, 1 H), 6.83 (d, 4 H), 7.23–7.40 (m, 9 H), 7.63 (d, 1 H), 9.19 (s, broad, 1 H).

The other three nucleoside derivatives were obtained in a similar manner.

EXAMPLE 2

Synthesis of Phosphoramidites

Synthesis of a (2-cyanoethyl) N,N-diisopropylphosphoramidite (5) (B=T). The thymidine derivative (4 ) (1.50 g, 1.53 mmol) was dried by coevaporation with toluene (20 ml) and dissolved in anhydrous dichlormethane (15 ml). To this magnetically stirred solution dry triethylamine (0.85 ml, 6.0 mmol) was added followed by 2-cyanoethyl-N,N-diisopropylaminophosphochloridate (710 mg, 3.0 mmol). After 15 min stirring at 20° C., TLC showed consumption of all starting material and formation of a single product. The reaction mixture was quickly partitioned between saturated aqueous sodium bicarbonate and dichloromethane and extracted with dichlormethane (2×50 ml). The residue obtained after evaporation of the organic phase was dried by coevaporation with toluene and purified on a short silica gel column, prepared and eluted with CH$_2$ Cl$_2$/Et3N 9/1 v/v. Fractions containing the desired product were combined, evaporated in vacuo, coevaporated with dry triethylamine, and dried in high vacuum to yield 1.57 g (87% ) of an oil; $^{31}$P-NMR (CDL$_3$+2 drops of triethylamine) 148.61 ppm.

The remaining amidites were prepared as above.

EXAMPLE 3

Figure 1:
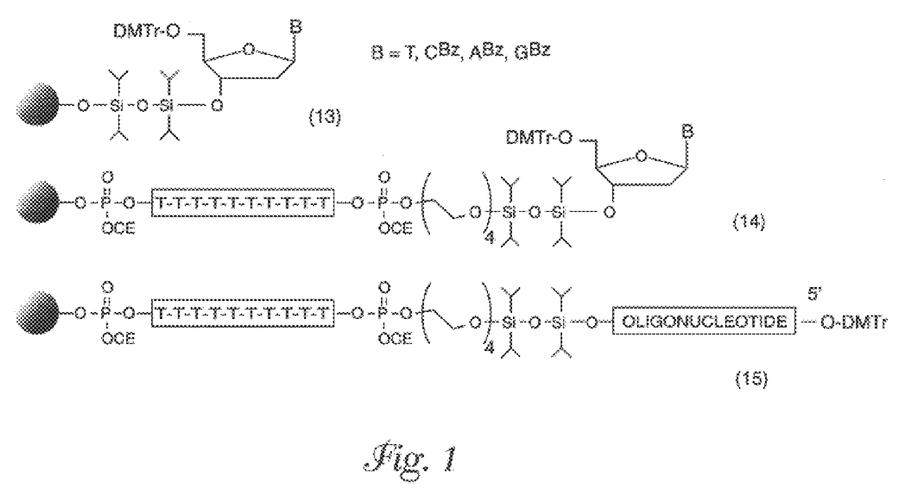
FIG. 1 shows starting points for oligonucleotide synthesis with or without an oligonucleotide linker (14 and 13, respectively) and the support after accomplished synthesis (15).
Figure 2A:
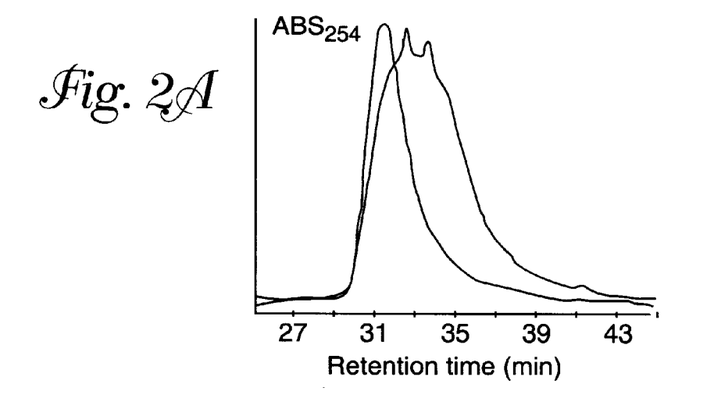
Figure 2B:
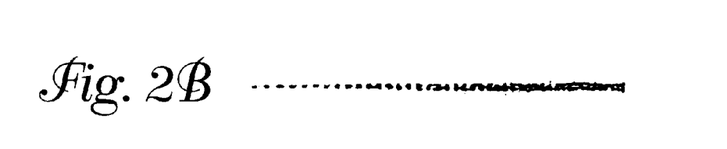
Figure 2C:
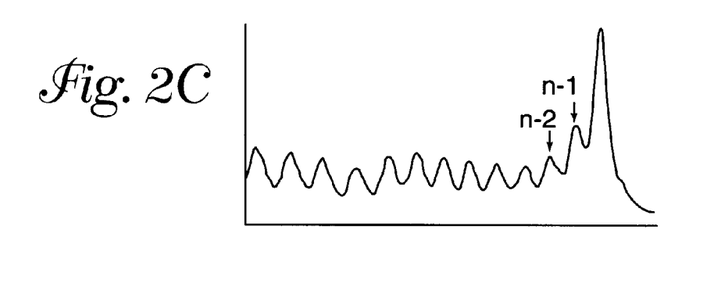
Figure 2D:
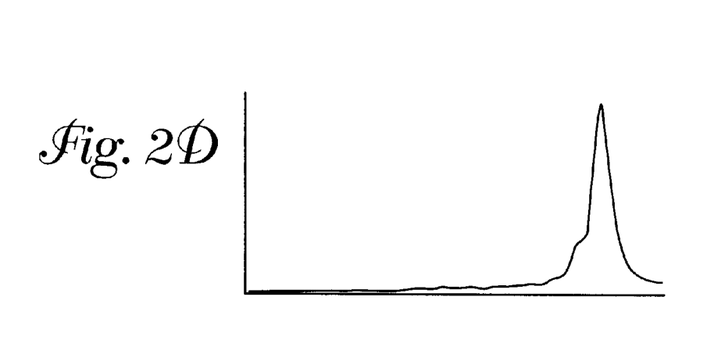

Construction of Hydroxyalkyl-Derivatized CPG Support (14) (See FIG. 1)

Asymmetrical anhydride (11) (see Scheme 2) was used for derivatization of aminopropylated CPG. The substitution level was analyzed based on DMTr cation release as described in [Gait, (ed) (1984) Oligonucleotide synthesis; a practical approach.. IRL Press]. CPG derivatized to the extent of 28 $\mu$mol/g was selected for further experiments. Several DNA synthesis columns were loaded with this support (ca 10 mg each), and they were subjected to 10 coupling cycles with a standard thymidine amidite, followed by coupling of one of the nucleoside amidites (5) to obtain support (14) . These supports were used for oligonucleotide synthesis.

EXAMPLE 4

Construction of Derivatized Polystyrene Support

Method A: Construction of support (13), FIG. 1.

Several portions of a cross-linked polystyrene support (Mono R) (from Pharmacia) (0.50 g) were dried by coevaporation with pyridine and suspended in pyridine (2 ml). Different volumes of compound (3) (Scheme 1), prepared at a 1 mmol scale in pyridine (10 ml), see Example 1 above, were added to the above suspensions and the mixtures were shaken at 20° C. for 2 hr. All activated sites that cool theoretically form in the reaction of unreacted (2) with the solid support were quenched by the addition of methanol (5 ml). After 1 hr shaking, the mixture was filtered, dried by washing with dry pyridine, and transferred back to the stoppered flask, where unreacted hydroxyl groups were capped with Ac$_2$O/DMAP (4-dimethylaminopyridine)/pyridine for 2 hrs. The amounts of DMTr thymidine bound directly to the support via the disiloxyl bond (13) were checked spectrophotometrically as above.

Method B: Construction of support (14), FIG. 1

A polystyrene support (10 mg), derivatized with hydroxyalkyl groups, was packed into cassettes for synthesis of oligonucleotides on a Gene Assembler Plus instruments (Pharmacia). These packed supports were subjected to one coupling cycle using a standard thymidine amidite that was 5 time more diluted than recommended in standard coupling procedures. The support was extensively (capped 10 min) on the machine operating in a manual mode. Under the above conditions the DMTr release experiments gave values comparable to those form the orginal 0.2 µmol supports. All thymidine nucleotides, followed by coupling of the appropriate amidite (5) from Example 2 above. These couplings were performed using standard amidite concentrations and synthesis protocols.

EXAMPLE 5

Solid-Phase Synthesis of Oligodeoxynucleotides (15), FIG. 1

Using the ABI 394 DNA Synthesizer and CPG supports

The CPG support (14) described above was used for oligonucleotide synthesis. All couplings were performed using amidites protected by a benzoyl group at the exocyclic amine functions, under conditions recommended by the manufacturer for 0.2 µmol scale synthesis, except that nucleoside amidites were used at half the recommended concentrations. The final DMTr groups were left on the synthesized oligonucleotide.

Synthesis on a Gene Assemble (Pharmacia) using the polystyrene support

All syntheses were done at the 0.2 µmol scale using PAC amidites (Pharmacia Biotech AB), according to the manufacturer's instructions and without any changes in the recommended amidite concentrations. Supports constructed according to methods A (13) or B (14) in Example 4 above were used, see also FIG. 1.

Normal scale reaction of standard nucleoside amidites or the modified amidite (5) with hydroxyalkyl-polystyrene support resulted in a very high loading. Quantitative analysis of the released DMTr-group revealed loadings of as much as 250 to 290 µmol/g. Also functionalizations involving an excess of reagent (3) gave a relatively high degree of substitution. Reaction of 0.5 mmol of (3) per 1 g of solid support at 20° C. for 2 hrs resulted in a support loaded at 180 µmol/g. These comparatively large numbers were a consequence of the high density of hydroxyl groups on the support and of the high reactivity of the reagents used. Such highly derivatized supports are valuble for large-scale synthesis of short therapeutic oligonucleotides. For the synthesis of relatively long oligonucleotides measures had to be taken to limit this high degree of substitution. A satisfactory loading (38 µmol/g) could be obtained by using only 0.1 mmol of (3) per 1 g of support. Several-fold dilution of (5) method for direct incorporation of (5) on the polystyrene support. The same dilution method was applied to the first standard amidite used for synthesis of the polystyrene version of the support (14). All coupling reactions described above were followed by and extensive capping procedure to block any unreacted hydroxyl groups.

EXAMPLE 6

Deprotection and Purification of the Synthetic Oligodeoxynucleotides

Different deprotection procedures were used, depending on the type of support that was applied in the synthesis.

CPG-anchored oligonucleotides. A syringe filled with a mixture of $Et_3EtN/EtOH$ 1:1 v/v was connected to a cassette containing support for oligonucleotide synthesis. Treatment of the support with base proceeded for 3 hrs at 20° C., with the occasional addition of a new aliquot of the solvent to the cassette. The support was washed with ethanol (2 ml), water (2×2 ml), dried with acetonitrile (3×2 ml), and after opening the cassette the solid support was transferred to a Sarstedt screw-lock tube. Tetrabutyl ammonium fluoride (TBAF) 0.5 M in dry tetrahydrofuran (THF) (200 µl) was added and the mixture was incubated for 4 hr at 20° C. The cleavage of the disiloxyl linker could alternatively be done using 200 ml of 0.5 M TBAF in dry DMF at 65° C. for 30 min. Concentrated aq. $NH_3$ (2 ml) was introduced and the mixture was placed in a 65° C. oven for 12 hrs. After partial concentration the oligonucleotide was desalted on a NAP 10 Sephadex column (Pharmacia Biotech AB) and analyzed by HPLC on a RP 18 column. Preparative runs were done on an FPLC using a reversed-phase Pep RPC column. Care was taken not to fractionate the hydrophobic trityl-containing product but rather to collect the whole peak, which closely resembles separations on disposable RP cartridges (Sep-Pak, $C_{18}$, Waters, USA). After evaporation, the final removal of the DMTr groups was done using 80% aq. acetic acid for 20 min at 20° C., with subsequent evaporation of the acid. alternatively, oligonucleotides phosphorylated at their 5'-position by the Tr-S phosporylating reagent were finally deprotected according to the published procedure [Connoly, (1987) Tetrahedron Lett., 28(4), 463–466].

Polystyrene support-anchored oligonucleotides. After completed synthesis, the support was transfered from the cassette into a Sarstedt tube and subjected to treatment with concentrated aq. $NH_3$ for 90 min at 65° C. After cooling, the particles were briefly centrifuged and the upper liquid phase was removed. The solid-support was washed 3 times with 2 ml of water and dried by washing with acetonitrile. Two hundred µl of 0.5 M TBAF in THF was added and the mixture was incubated for 4 hr. Finally, the mixture was diluted with 0.8 ml water and the oligonucleotide was desalted on a NAP 10 Sephadex column. The further deprotection and purification steps follow exactly those described for CPG-bound oligonucleotides.

EXAMPLE 7

Electrophoretic Analysis of Oligonucleotides

Oligonucleotides to be analyzed electrophoretically were labelled with $^{32}p$ at their 5'-end using polynucleotide kinase in a 50 µ l reaction volume of 50 mM KAc, 10 mM $MgCl_2$, 10 mM Tris-HAc (pH 7.5), 10 µCi (g-$^{32}$P) ATP (3000 Ci/mmol), and 10 U polynucleotide kinase (Amersham) at 37° C. for 30 min. The labelling reaction was stopped by desalting on a Sephadex G-50 spin column, followed by incubation at 65° C. for 5 min. All oligonucleotides analyzed electrophoretically in this study were synthesized with a 5'-phosphate to ensure that cleaved apurinic oligonucleotides would label with the same efficiency as the full-length molecules. After separation on a denaturing 6% polyacrylamide gel the radioactivity was recorded by autoradiography (Amersham Hyperfilm) or, for quantitative measurements of band intensities, scanned on a Phosphorimager instrument (Molecular Dynamics).

EXAMPLE 8

Purine-Rich Oligonucleotides

The risk of depurination of an oligonucleotide increases with the number of purines and the total length of the oligonucleotide. An increased amount of purines in an Oligodeoxynucleotide gives a high probability of its depurination and the following brake-down. To show the capability of the new method to eliminate these short sequences, two 81-mer (AG) $_{40}$T sequences were synthesized in parallel using standard and novel CPG-based supports (14), respectively. Partially deprotected 5'-DMTr-substituted oligonucleotides were analyzed and isolated by HPLC. Both products were detritylated, 5'-$^{32}$p kinased and electrophoretically separated on a denaturing polyacrylamide gel. The results, presented in FIG. 2 show the superiority of the invention compared to prior art. This superiority could already be anticipated by comparing the shapes of the HPLC chromatogram (A). the much broader peak obtained in the standard synthesis reflects the presence of the shorter and therefore more hydrophobe tritylated fragments. It is clear from the scanned presentation of the gel separation (B) that the product synhesized according to the present invention is practically free of all truncated and depurinated sequences. Moreover, this material contains substantially lesser amount of n-1 fragments [(D) compared to (C)].

EXAMPLE 9

Circularization of a Padlock Probe

A 91-mer oligonucleotide (M13C91: 5'-P-GCCTGCAGGTCGACTCTAGA (T)$_{50}$ CGGCCAGTGCCAAGCTTGCA-3') were synthesized according to the invention in order to test how it would work as a padlock probe [Nilsson et al (1994), supra] that is able to circularize in presence of an oligonucleotide template (Ml350comp: 5'-TTTTTCTAGAGTCGACCTGCAGG CATGCAAGCTTGGCACTGGCCGTTTTT-3') and a DNA-ligase. The ligation reaction was performed using 0.3 pmol of 5'-labelled probe and 5.5 pmol of template in a volume of 10 µl 20 mM Tris-HCl (pH 8.3), 25 mM KCl, 10 mM MgCl$_2$, 1 mM NAD, 0.01% Triton X-100 and 10 U of Tth DNA ligase. The sample were subjected to one, two or three cycles of 94° C. for 15 seconds and 55° C. for 10 min. The reactions were cooled on ice and stopped by adding 10 µmM EDTA followed by a incubation at 65° C. for 10 min. The reactions were analyzed on a denaturing polyacrylamide gel as above.

Figure 3:
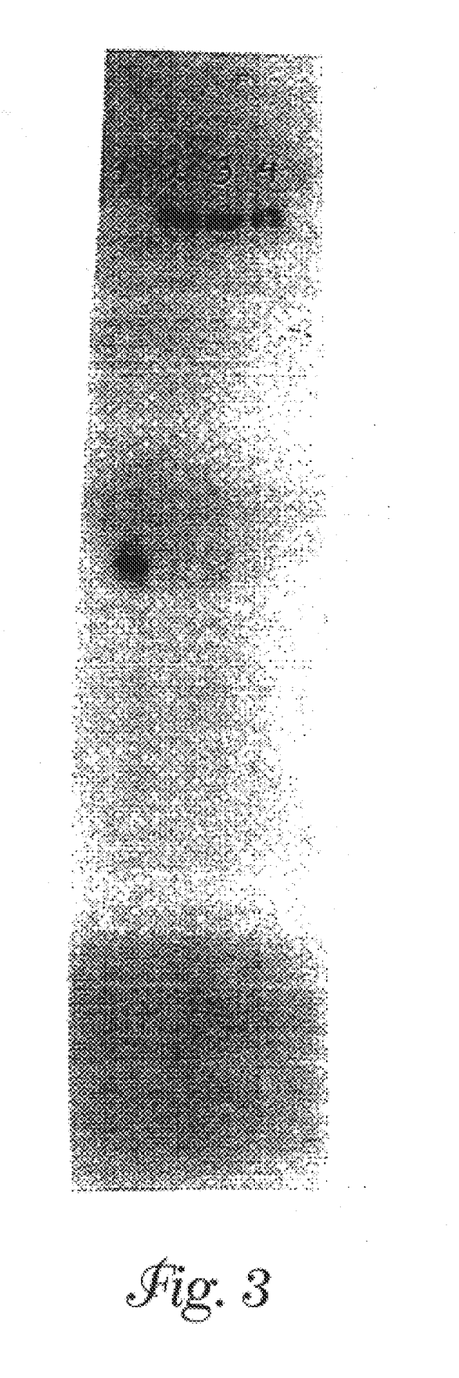

The result of the ligation is shown in FIG. 3 which clearly shows that all full-length oligonucleotides are ligatable as well as most of the n-1 products, as would be expected if the deletions were evenly distributed throughout the sequence. It also shows the presence of many shorter products that are ligatable and thus having intact 5'- and 3'- ends thereby revealing deletion events of more than one nucleotide. Consequently, all nonligating shorter sequences must contain deletions that prevent effective hybridization to the targed DNA.

The present invention delivers products free of truncated and post-depurination cleaved fragments, morover, the isolated products contain much less n-1 fragments. The amount of this n-1 material was estimated, in a study performed on a short 5-mer sequence and using a standard synthesis protocol ([Iyer et al, (1995), 14(6) 1349–1357]), to be roughly 3 to 5%. By applying pre-cap procedure according to Iyer et al and short contact time of ammonia with the CPG support it was possible to lower this figure to 1.5 to 2%. In contrast, in an experiment according to the present invention for synthesis of a 20-mer using CPG support (14), the amount of contamination n-1 sequences was found to 1.9%.

The support system of the present invention is not limited to the solid-phase synthesis of oligonucleotides described above. Another contemplated possibility is to use it as a linker between support and hydroxyl containing components in the combinatorial chemistry ([Plunkett et al, (1995), J. Org. Chem., 60(19), 6006–6007]).

What is claimed is:

1. A support system for synthesizing oligomers comprising a hydroxyl-containing compound bound to a support via a disiloxyl linkage.

2. The support system of claim 1, wherein said hydroxyl-containing compound is a nucleoside.

3. The support system of claim 1 wherein said hydroxyl-containing compound is non-nucleoside hydroxyl-containing compound.

4. A support system for synthesizing oligomers comprising the formula:

wherein
Supp is a solid support;
B is a nucleoside or deoxynucleoside base;
$R_1$ is a first protecting group;
$R_2$ is —H, —OH or $OR_7$, wherein $R_7$ is a second protecting group;
$R_3$, $R_4$, $R_5$ and $R_6$ are each, independently or together, alkyl, aryl, cycloalkyl, alkenyl, aralkyl, cycloalkylalkyl, alkyloxy, aryloxy, cycloalkyloxy, alkenyloxy or aralkyloxy;
$(p\text{-}Y)_n$ and $(p\text{-}Z)_m$ are oligophosphotriesters linkers, wherein Y is a nucleoside, and
Z is a rest of a diol;
A is an aliphatic or aromatic group;
X is an anchoring group;
n is an integer ranging from 0 to 50;
k, l and m are each 0 or 1;
wherein when m and n are 0, then k and l are 0, and wherein when m is 1 then k is 0 and X is either O or S.

5. The support system of claim 4, wherein B is adenine, guanine, cytosine, uracil, thymine, or inosine.

6. The support system of claim 4, wherein $R_1$ is trityl, monomethoxy trityl, dimethoxytrityl, pixyl or higher alkoxy-substituted trityl-protecting group.

7. The support system of claim 4, wherein $R_7$ is tertbutyldimehylsilyl, methoxytetrahydropyranoyl, tetrahydropyranol, methyl or allyl.

8. The support system of claim 4, wherein in $R_3$, $R_4$, $R_5$ and $R_6$ are isopropyl.

9. The support system of claim 4, wherein X is O, S or an amide.

10. The support system of claim 4, wherein n ranges from 0 to 10.

11. The support system of claim 4, wherein m and n are 0.

12. The support system of claim 4, wherein m is 1 and n is 0.

13. The support system of claim 4, wherein m is 0 and n is greater than or equal to 1.

14. The support system of claim 4, wherein m is 1 and n is greater than or equal to 1.

15. A method for synthesizing an oligonucleotide, comprising the steps:
  a. providing a support system comprising a hydroxyl-containing compound bound to a support via a disiloxyl linkage; and
  b. condensing a 5'-protected nucleoside phosphoramidite on said support system.

* * * * *

UNITED STATES PATENT AND TRADEMARK OFFICE
CERTIFICATE OF CORRECTION

PATENT NO. : 6,291,669 B1
DATED : September 18, 2001
INVENTOR(S) : Marek Kwiatkowski, Mats Nilsson and Ulf Landegren It is certified that error appears in the above-identified patent and that said Letters Patent is hereby corrected as shown below:

<u>Column 16,</u>
Line 5, please delete "tertbutyldimehylsilyl" and insert -- tetrabutydimethylsilyl -- therefor.

Signed and Sealed this

Fifth Day of March, 2002

*Attest:*

*Attesting Officer*

JAMES E. ROGAN
*Director of the United States Patent and Trademark Office*

SEQUENCE LISTING

<160> NUMBER OF SEQ ID NOS: 2

<210> SEQ ID NO 1
<211> LENGTH: 90
<212> TYPE: DNA
<213> ORGANISM: Artificial Sequence
<220> FEATURE:
<223> OTHER INFORMATION: circularization probe

<400> SEQUENCE: 1
gcctgcaggt cgactctaga tttttttttt tttttttttt tttttttttt tttttttttt    60
tttttttttt cggccagtgc caagcttgca                                      90

<210> SEQ ID NO 2
<211> LENGTH: 50
<212> TYPE: DNA
<213> ORGANISM: Artificial Sequence
<220> FEATURE:
<223> OTHER INFORMATION: circularization probe

<400> SEQUENCE: 2
tttttctaga gtcgacctgc aggcatgcaa gcttggcact ggccgttttt               50